US005253657A

United States Patent [19]

Butterfield

[11] Patent Number: 5,253,657

[45] Date of Patent: Oct. 19, 1993

[54] HARNESS UTILIZED IN SHIFTING A POSITION OF A HUMAN WEARER

[76] Inventor: Ida M. Butterfield, 1026 Buchanan, Yuba City, Calif. 95991

[21] Appl. No.: 874,115

[22] Filed: Apr. 24, 1992

Related U.S. Application Data

[63] Continuation-in-part of Ser. No. 821,476, Jan. 14, 1992.

[51] Int. Cl.[5] .......... A61G 15/00; A61F 5/37

[52] U.S. Cl. .......... 128/845; 128/875

[58] Field of Search .......... 128/871-876, 128/845; 119/96; 2/45; 294/140, 149, 150, 153, 156, 157

[56] References Cited

U.S. PATENT DOCUMENTS

| | | | |
|---|---|---|---|
| 1,050,257 | 1/1913 | Trigg . | |
| 1,310,958 | 7/1919 | O'Connor | 128/875 |
| 1,711,864 | 5/1929 | Whidden . | |
| 1,816,262 | 7/1931 | Ritter . | |
| 2,062,586 | 12/1936 | Lawrence . | |
| 2,102,281 | 12/1937 | Pringle . | |
| 2,212,746 | 8/1940 | Nunn . | |
| 2,568,304 | 9/1951 | Schoenbrun . | |
| 2,758,769 | 8/1956 | Nunn et al. . | |
| 2,812,123 | 11/1957 | Girton | 294/150 |
| 2,900,976 | 8/1959 | Kilmer . | |
| 2,956,541 | 11/1960 | Ball . | |
| 3,046,982 | 7/1962 | Davis | 128/875 |
| 3,191,599 | 6/1965 | Kendell | 128/875 |
| 3,458,878 | 8/1969 | Combs . | |
| 3,563,208 | 2/1971 | Nero | 119/96 |
| 3,669,107 | 6/1972 | Posey . | |
| 3,884,225 | 5/1975 | Witter . | |
| 3,889,668 | 6/1975 | Ochs et al. . | |
| 4,024,876 | 5/1977 | Penrock | 623/7 |
| 4,308,629 | 1/1982 | Freemon | 119/96 |
| 4,396,013 | 8/1983 | Hasslinger . | |
| 4,569,095 | 2/1986 | Holling . | |
| 4,641,642 | 2/1987 | Williams | 128/875 |
| 4,655,207 | 4/1987 | Ellis . | |
| 4,666,017 | 5/1987 | Zimmerman | 119/96 |
| 4,667,624 | 5/1987 | Smith . | |
| 4,675,925 | 6/1987 | Littleton . | |
| 4,759,311 | 7/1988 | Boyle . | |
| 4,788,941 | 12/1988 | Villenuve . | |
| 4,793,008 | 12/1988 | Johansson . | |
| 4,860,560 | 8/1989 | Lundelius | 128/876 |

*Primary Examiner*—Michael A. Brown
*Attorney, Agent, or Firm*—James M. Ritchey

[57] ABSTRACT

A device employed by a user for shifting the position of a human wearer comprises an adjustable body belt, attached shoulder strap with an associated handle, and a pair of side handles attached to the belt. The belt is fitted by the user around the wearer's upper body, encircling the torso and arms. The shoulder strap with its associated handle or the side handles on the belt are used to shift the position of the wearer.

9 Claims, 3 Drawing Sheets

HARNESS UTILIZED IN SHIFTING A POSITION OF A HUMAN WEARER

This application is a continuation in part of Ser. No. 07/821,476, filed on Jan. 14, 1992.

1. FIELD OF THE INVENTION

This invention relates to a device for shifting the position of a person fitted with the subject harness. More specifically, the subject device comprises a graspable shoulder strap and side handles coupled to a torso surrounding body belt. Several shifting motions are made easier for a user by fitting a wearer with the subject device, including: elevating a medical patient's upper body or torso off the surface of an underlying support so that a chest board may be inserted between the back of the patient and the underlying support; dragging a wearer fitted with the subject harness by means of the associated handles; rotating or rolling a wearer by means of the side handles; and similar actions.

2. DESCRIPTION OF THE BACKGROUND ART

Traditionally, moving a person incapable of self movement or restricted to limited movement by reasons such as physical disability, age, injury, and the like has presented extreme difficulties for individuals with insufficient strength or leveraging ability. A common example is the necessity of inserting a chest board (an essentially rigid board that aids in insulating a patient from a supporting surface and provides a firm platform on which to perform CPR or similar procedures to the wearer or patient's exposed chest area) between a patient's back and an underlying supporting surface that required an unsuitable and often dangerous amount of critical time and effort. A medical staff member needed to grasp the wearer or patient and often struggle (especially if the patient was heavy and the staff member physically small) to lift the patient and then push the board into position. No suitable mechanical aids were available to assist the staff member in this difficult lifting and positioning process. Various harness devices exist for restraining or moving a person, but these prior art devices require ready access to the wearer's back region for fitting and usually demand the wearer's arms fit through small opening, neither of which are practical for a critically ill and possibly heavy wearer or patient.

U.S. Pat. No. 1,050,257 relates an elastic shoulder brace.

U.S. Pat. Nos. 1,310,958, 1,711,864, 1,816,262, 2,102,281, 2,212,746, 2,568,304, 2,758,769, 4,308,629, 4,666,017, 4,667,624, and 4,759,311 all disclose harnesses used with children for safety or restraining purposes.

U.S. Pat. Nos. 2,062,586, 4,655,207, and 3,669,107 present devices employed in restraining individuals.

U.S. Pat. Nos. 2,900,976, 3,458,878, 3,884,225, 3,889,668, 4,396,013, 4,569,095, 4,641,642, 4,675,925, and 4,793,008 all disclose medically related devices for moving, aiding, or securing patients.

U.S. Pat. Nos. 2,812,123, 2,956,541, and 4,273,215 describe and claim sports related harnesses.

U.S. Pat. No. 4,788,941 discloses a safety belt with multiple latches.

SUMMARY OF THE INVENTION

An object of the present invention is to provide a device for quickly raising a patient's upper body off the surface of an underlying support to permit a chest board to slide between the back of the wearer or patient and the support surface.

Another object of the present invention is to produce an inexpensive, compact, and optionally disposable device for assisting in moving a wearer into a shifted position by lifting, rotating, sliding, and the like.

An additional object of the present invention is to create a lifting aid that permits a single individual to lift the upper body of an heavy wearer or patient far enough above a supporting surface to be able to slide a chest board between the patient and the supporting surface.

Yet another object of the present invention is to furnish a wearer or patient lifting device that may be fitted rapidly to a wearer or patient that is lying back down on a supporting surface without requiring access to the wearer or patient's back area.

Yet still an additional object of the present invention is to provide a harness that includes color coded handles that emphasize the position to grasp for movement.

Yet an additional object of the present invention is to present a harness that is fitted to a person within a confined space, say an airplane seat, and then used to move that person to a more open area, say an airplane isle.

The subject invention, a harness, comprises an adjustable upper body belt secured to a lifting shoulder strap having an handle. The belt having two end regions is equipped with coupling means to permit the user to reversibly mate the end regions to each other to generate a linked structure (usually of approximately circular or oblong shape) of adjustable perimeter size. The lifting shoulder strap having a strap end domain at each of its two ends is attached via one of the strap end domains to the belt proximate the midpoint of the belt, between the belt end regions. Attached at the second strap end domain is a handle. Attached to the body belt is at least one addition handle and preferably two handles that are used for turning, twisting, sliding, and similar movements.

For use with a chest board, a user of the subject device positions a wearer or patient so that the patient's back is against the surface of a supporting structure, floor, or earth. The belt is slipped under the upper body of the wearer or patient's body and the coupling means mated over the wearer or patient's exposed chest area or arms to produce a securely linked and fitted encircling belt harness that surrounds the wearer or patient's upper body, including the arms. Since the coupling means links over the chest area or arms of the wearer or patient, access to the wearer or patient's back area is not required in fitting the harness, thus minimizing the need of moving the wearer or patient. The lifting shoulder strap runs from the belt attachment point under the wearer or patient and past a shoulder to expose the associated handle. By grasping the shoulder strap handle and pulling in a generally upward direction, a user has the necessary leverage to raise a wearer or patient's upper body off the underlying surface. Once raised, the user slips a chest board, or equivalent device, under the wearer or patient and lowers the wearer or patient on the chest board for further medical treatment.

As indicated above, in addition to use with a chest board, the subject device is used for general movements of a wearer by a user, including: dragging, lifting, twisting, rotating, turning, restraining, and the like.

Other objects, advantages, and novel features of the present invention will become apparent from the detailed description that follows, when considered in conjunction with the associated drawings.

DESCRIPTION OF THE PREFERRED EMBODIMENT

Figure 1:
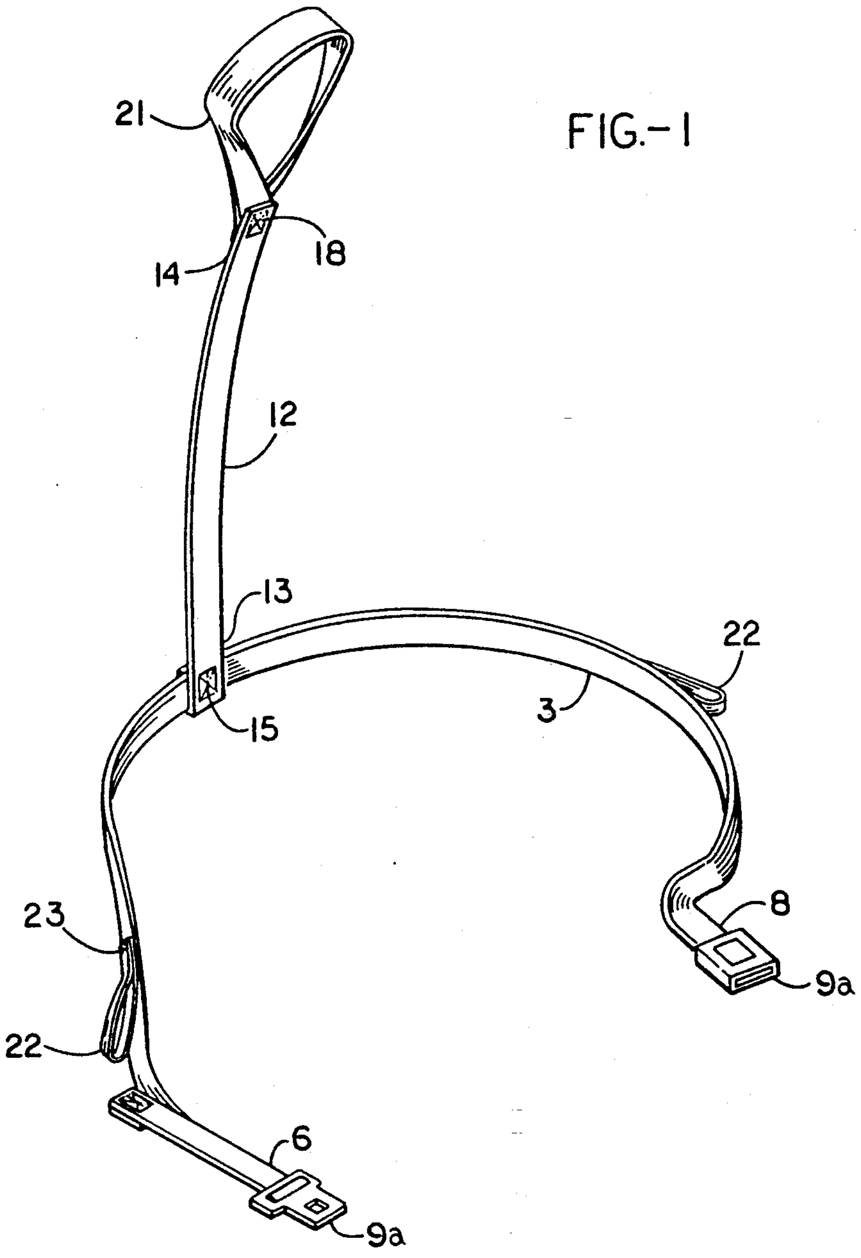
FIG. 1 is a perspective illustration of the subject device.
Figure 2:
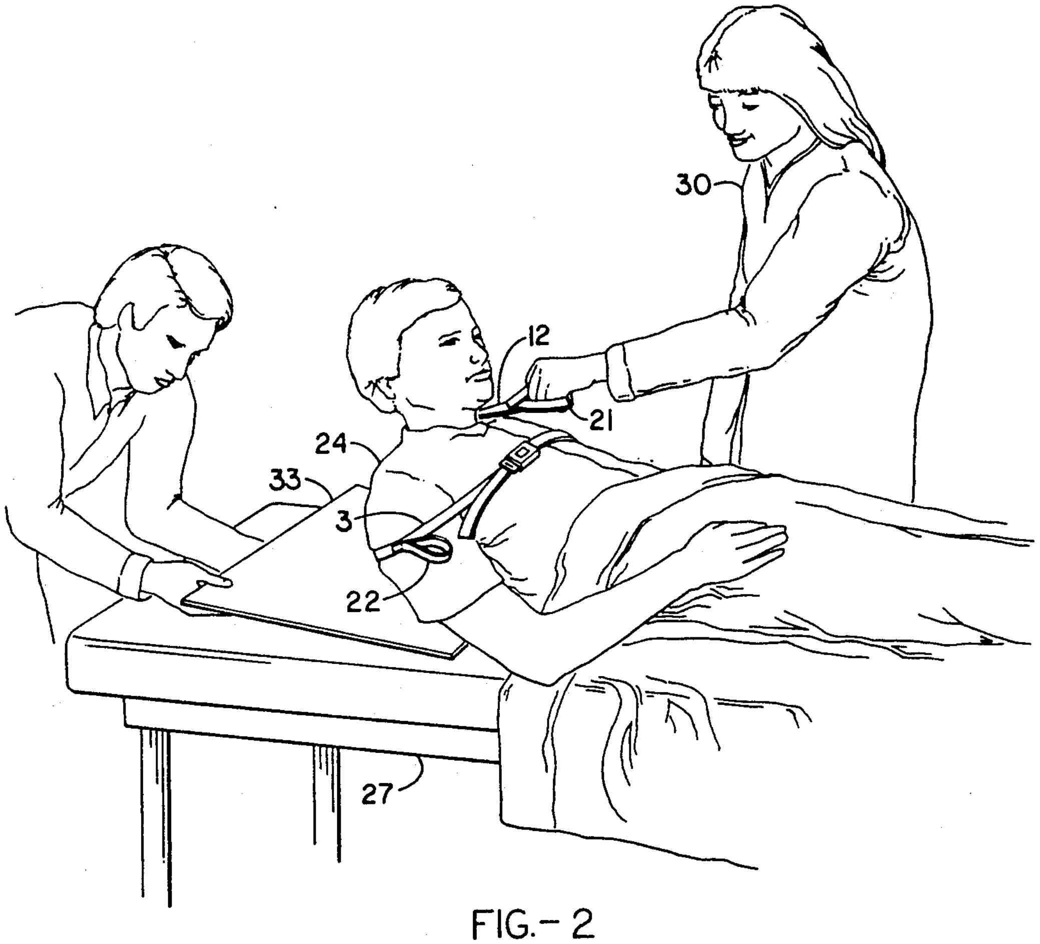
FIG. 2 is a perspective illustration of the subject lifting device being employed by a user on a wearer or patient to lift the wearer or patient's upper body off the underlying surface.
Figure 3:
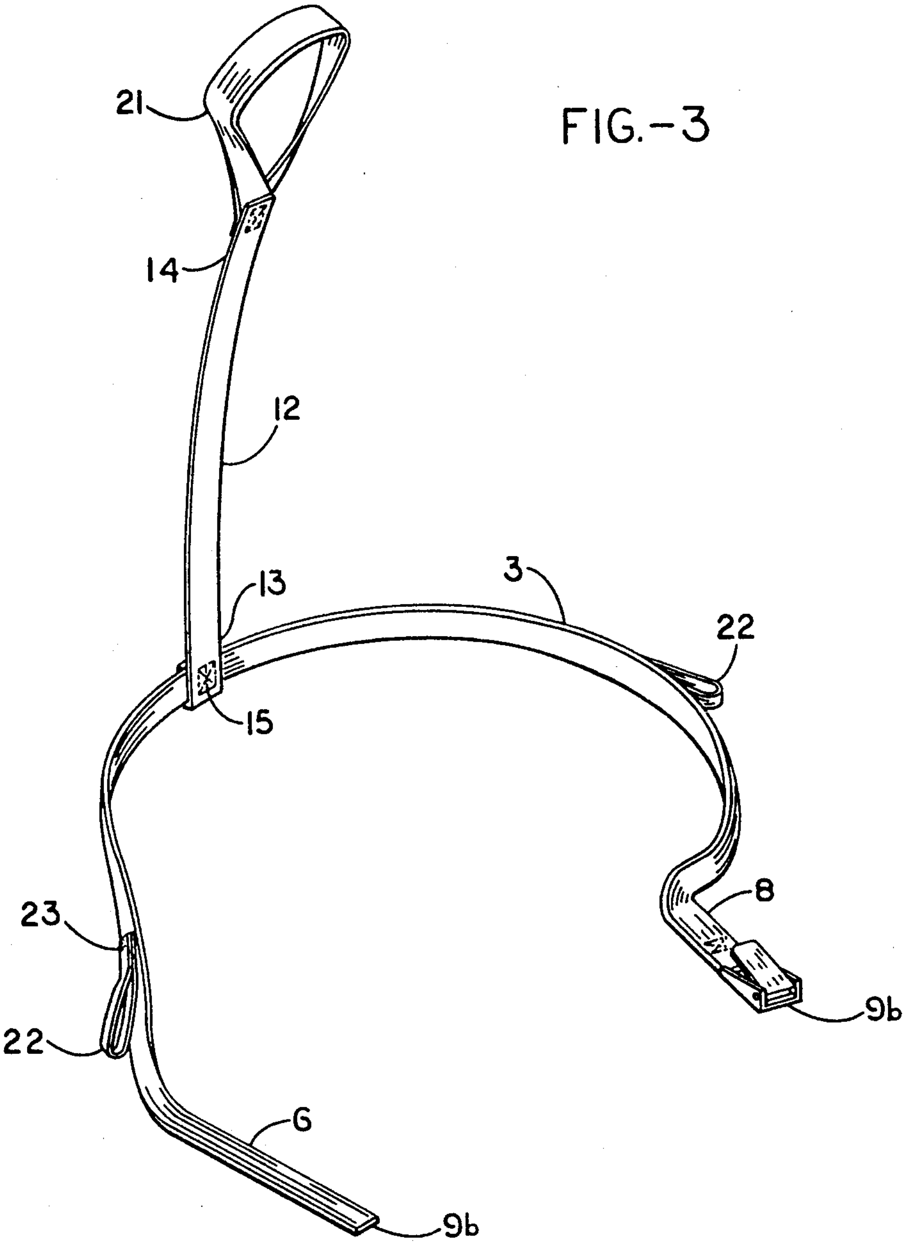
FIG. 3 is an additional embodiment of the subject device.

Referring now to FIGS. 1, 2, and 3 there are shown two preferred embodiments of a harness 1 of the subject invention. This device is for moving a wearer, often for raising the upper body of a patient off the surface of an underlying support to permit the insertion of a chest board between the patient's back and the surface of the underlying support. In addition to direct medical use, use of the subject invention is envisioned at home or in out-patient facilities to assist a care provider in moving a motion restricted individual.

The subject invention, a wearer or patient harness 1, as illustrated in particular in the FIGS. 1 and 3, comprises a body belt 3 having first 6 and second 8 end regions. The belt 3 is a band-like strip preferably of flattened and elongated rectangular proportions constructed from a sturdy material capable of withstanding the forces exerted by the heaviest wearer or patient. Suitable sturdy materials are woven or braided nylon or similar polymer, cloth, leather, or equivalent substances. The material should not have any appreciable stretch. Although the body belt 3 may be of any cross-sectional area, the flattened form is preferred. This flattened form permits a user to slip the belt 3 easily under the back of a reclining wearer or patient without the need of having free access to the wearer or patient's back area.

For adjustably fastening and fitting the body belt 3 about the upper body of a wearer or patient, around the upper portion of the torso, including the shoulder area of the arms, coupling means 9*a* (see FIGS. 1 and 2) or 9*b* (see FIG. 3) are associated with the first 6 and second 8 belt end regions. The coupling means (9*a* and 9*b* represent two preferred versions, but equivalent means are contemplated to be within the realm of this disclosure) forms a reversible mating link between the two belt end regions 6 and 8. The coupling means 9*a* and 9*b* serves to secure the belt 3 about a wearer or patient to form a reversibly linked structure (usually of approximately circular or oblong shape) of adjustable perimeter size. To facilitate a rapid fitting the coupling means 9*a* and 9*b* is readily adjustable to fit the physical size of the wearer or patient. As shown in FIGS. 1 and 2, the coupling means 9*a* is (as one depicted exemplary embodiment) a seat belt-like latch with mating male and female components, one associated with each end region 6 and 8. These mating components are positioned, relative to the belt 3 and the wearer or patient, to mate on the easily accessible chest or side areas of the wearer or patient. As with a typical seat-belt in an airplane, the latch components are mated and the appropriate end of the belt 3 drawn tight to fit around the wearer or patient.

Coupling means 9*b* (see FIG. 3) comprises an unmodified first belt end region 6 and a latch secured to the second belt end region 8. The first belt end region is inserted into the latch and the latch is clamped down by a leveraging action to engage and hold the belt closed.

In addition to the depicted seat belt-like coupling means 9*a* and 9*b*, other functionally equivalent coupling means may be employed, including a Velcro® mating pair, snaps, hooks and eyes, and like devices associated with the belt end regions 6 and 8. In particular, for a Velcro® mating pair having two members, each belt end region 6 and 8 is attached to one of the mating members. The length of the Velcro® mating members is sufficient to allow the user to adjust the belt 3 to fit around the wearer or patient.

A shoulder strap 12 terminating in first 13 and second 14 strap end domains is attached to the belt 3 via the first strap end domain 13. As with the belt 3, the shoulder strap 12 is preferably a flattened and elongated rectangular band of sturdy material of sufficient structural strength to easily withstand the weight of the heaviest wearer or patient. The shoulder strap 12 is connected to the belt 3 at a belt attachment point 15. Preferably, this attachment and the other attachments between the components of the subject device are permanent attachments (except for the belt coupling means) that withstand any reasonable amount of moving force without becoming detached. Although other angles are contemplated to be within the realm of this disclosure, the angle between the belt 3 and the shoulder strap 12 long axes is approximately 90°, thereby generating a T-like attachment. The belt attachment point 15 is between the first 6 and second 8 belt end regions, preferably proximate the long axis midpoint of the belt 3. The length of the shoulder strap 12 is variable, usually between two and five feet and preferably about two to three feet.

Attached via the second strap end domain 14 at an handle attachment point 18 is a handle 21. As long as the handle 21 may be grasped quickly and easily by a user of the subject device, this handle 21 may be of varied structural design. Pictured in FIGS. 1 and 2 is a preferred strap-like loop handle 21 that is strong and readily grasped, in addition to being economical to produce.

Materials like those used to produce the belt 3 are appropriate for fabricating the shoulder strap 12 and handle 21. To attach the shoulder strap 12 to the body belt 3 and the handle 21 to the shoulder strap 12, standard methods are employed such as stitching, riveting, gluing, heating, braiding, or equivalent procedures that are, preferably, permanent in nature, as indicated above.

FIG. 2 illustrates the subject device being used to lift the upper body of a patient 24 off the surface of an underlying support 27 (the support being a bed, crash cart, table, floor, ground, and the like), however, for other movement uses the subject device is fit around a wearer in a similar manner. If the patient is situated with their back not in contact with the surface of the underlying support, the patient is positioned to have their back in contact with the surface of the underlying support. The belt 3 of the patient lifting harness is forced beneath the patient 24 for fitting. The belt 3 is forced under the patient's body at a body location proximate the wearer or patient's shoulders. Once the wearer or patient 24 has the belt 3 positioned under their back, the harness 1, specifically the belt 3, is fastened about the outer portion of the body to encircle the wearer or patient's upper body proximate the shoulders. The fastened belt 3 is adjusted by tightening or loosening the coupling means.

When the subject device is employed to move a wearer the user is any individual in need of assistance by the subject device. However, when a chest board is being used, a medical professional is usually the user. Specifically, a medical staff member 30 (e.g., a nurse, technician, physician, or similar individual), grasps the handle 21 and leverages the patient 24 into a partially raised position by exerting a pulling force strong enough to raise the patient's upper body sufficiently off the underlying surface to insert a chest board 33. Since a typical chest board 33 is approximately an inch thick, the height the upper body is raised above the underlying surface need not be great. Either a lone staff member 30 or a staff member with assistants (one assistant being shown in FIG. 2) inserts a chest board 33 beneath the wearer or patient. The patient 24 is lowered by easing the pulling force on the lifting harness 1, specifically the handle 21. The harness 1 is removed either before of after medical treatment.

Fabricated from the same sturdy, non-elastic materials as the shoulder strap 12 and the body belt 3 are side handles 22. Although one side handle 22 is contemplated, preferably two side handles 22 are securely attached to the body belt 3. One side handle 22 is attached to the body belt 3 between the shoulder strap first end domain 13 and the body belt first end 6. the other side handle 22 is attached to the body belt 3 between the shoulder strap first end domain 13 and the body belt second end 8. Each side handle 22 is connected to the belt 3 at a connection point 23.

In emergency situations time is often a critical factor in a patient's survival. Any assistance in decreasing the time required to complete a critical medical procedure is highly important. To speed the use of the subject device color coding of important elements is included. Preferably, each handle 21 and 22 is colored, usually red, to emphasize and indicate to the user exactly where to exert force.

Due to the possible presence of various harmful contaminants, communicable diseases, and the like in medical settings, the subject device can be fabricated from materials suitable for disposal or sterilization.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A harness employed by a user for shifting the position of a wearer, comprising:

a) a body belt constructed from sturdy material terminating in first and second end regions;

b) coupling means for reversible mating associated with said body belt, wherein when mated by said coupling means, said first and second body belt end regions form a reversibly linked structure about said wearer's body of adjustable perimeter size;

c) a shoulder strap having a minimum length of about two feet and constructed from sturdy material terminating in first and second end domains, wherein said shoulder strap first end domain is attached to said body belt between said body belt first and second end regions, proximate the long axis midpoint of said belt;

d) a first handle formed into a loop constructed from sturdy material attached to said shoulder strap second end domain; and e) a second handle formed into a loop constructed from sturdy material attached to said body belt.

2. A position shifting harness according to claim 1, further comprising a third handle constructed from sturdy material attached to said body belt.

3. A position shifting harness according to claim 1, wherein said first handle is color coded to emphasize its location for rapid grasping by said user.

4. A position shifting harness according to claim 1, wherein said second handle is color coded to emphasize its location for rapid grasping by said user.

5. A position shifting harness according to claim 2, wherein said third handle is color coded to emphasize its location for rapid grasping by said user.

6. A harness employed by a user for shifting the position of a wearer, comprising:

a) a body belt constructed from sturdy material terminating in first and second end regions;

b) coupling means for reversible mating associated with said body belt, wherein when mated by said coupling means, said first and second body belt end regions form a reversibly linked structure about said wearer's upper body proximate said wearer's shoulders of adjustable perimeter size;

c) a shoulder strap having a minimum length of about two feet and constructed from sturdy material terminating in first and second end domains, wherein said shoulder strap first end domain is attached to said body belt between said body belt first and second end regions, proximate the long axis midpoint of said belt;

d) a first handle formed into a loop constructed from sturdy material attached to said shoulder strap second end domain;

e) a second handle formed into a loop constructed from sturdy material attached to said body belt between said shoulder strap first end domain and said body belt first end; and f) a third handle constructed from sturdy material attached to said body belt between said shoulder strap first end domain and said body belt second end.

7. A position shifting harness according to claim 6, wherein said first handle is color coded to emphasize its location for rapid grasping by said user.

8. A position shifting harness according to claim 6, wherein said second handle is color coded to emphasize its location for rapid grasping by said user.

9. A position shifting harness according to claim 6, wherein said third handle is color coded to emphasize its location for rapid grasping by said user.

* * * * *